United States Patent [19]

Allwood et al.

[11] Patent Number: 5,108,758

[45] Date of Patent: Apr. 28, 1992

[54] DELAYED RELEASE FORMULATIONS

[75] Inventors: Michael C. Allwood, Fulbourn; David B. Archer, Little Melton; Stephen G. Ring, Hethersett, all of England

[73] Assignee: National Research Development Corporation, London, England

[21] Appl. No.: 438,488

[22] PCT Filed: May 25, 1989

[86] PCT No.: PCT/GB89/00581

§ 371 Date: Dec. 19, 1989

§ 102(e) Date: Dec. 19, 1989

[87] PCT Pub. No.: WO89/11269

PCT Pub. Date: Nov. 30, 1989

[30] Foreign Application Priority Data

May 26, 1988 [GB] United Kingdom ............... 8812490

[51] Int. Cl.$^5$ ............... A61K 9/22; A61K 9/36; C08B 31/00
[52] U.S. Cl. .................... 424/468; 424/479; 424/488; 424/489; 424/493; 424/499; 536/102
[58] Field of Search ........... 424/468, 489, 490, 493, 424/499, 418, 409, 488, 479, 4, 7.1; 427/3; 536/102

[56] References Cited

U.S. PATENT DOCUMENTS

| | | | |
|---|---|---|---|
| 3,499,962 | 3/1970 | Wurzburg | 424/35 |
| 4,695,467 | 9/1987 | Uemura et al. | 424/502 |
| 4,755,397 | 7/1988 | Eden et al. | 427/213.3 |

FOREIGN PATENT DOCUMENTS

| | | |
|---|---|---|
| 0118240 | 9/1984 | European Pat. Off. . |
| 1072795 | 6/1967 | United Kingdom . |
| 28900419 | 1/1989 | World Int. Prop. O. . |

OTHER PUBLICATIONS

Ring, S. G. et al., "Static and Dynamic Light Scattering Studies of Amylose Solutions", Macromolecules, 1985m 18, pp. 182–188.
J. Med. Chem. (1984), 27, 261–266, Friend & Chang.
Science (1986), 233, 1081–1084, Saffran et al.
Food Chemistry (1988), 28, 97–109, Ring et al.
Englyst & Cummings, "Cereals in a European Context", Ed. Morton, First European Conference on Food Science and Technology, Ellis Harwood, Chichester, England (1987), p. 221.
J. Am. Pharm. Assoc. (1959), 48, 244, Wagner et al.
Langlois & Wagner, "Production and Use of Amylose" in Starch Chemistry & Technology, vol. II, Eds. R. L. Whistler and E. F. Paschall, Academic Press (1965), p. 451.
"Work on Oral Insulin", article in Diabetes for the News (1987), published by Amec Laboratories Ltd., Bucks.
J. Sci. Food Agric. (1986), 37, 699–706, Englyst & MacFarlane.
J. Appl. Bacteriol. (1986), 60, 195–201, Englyst & MacFarlane.

*Primary Examiner*—Thurman K. Page
*Assistant Examiner*—G. S. Kishore
*Attorney, Agent, or Firm*—Nixon & Vanderhye

[57] ABSTRACT

Delayed release compositions comprising an active compound and glassy amylose. A variety of different types of active compound may be employed in the compositions. The compositions are particularly adapted for achieving the selective release of medicaments into the colon.

9 Claims, No Drawings

DELAYED RELEASE FORMULATIONS

The present invention relates to delayed release formulations, especially those in which the delayed release characteristic is due to a coating. The term "coating" is used herein to encompass coatings for solid supports and also capsules enclosing fluids and/or solids and the term "coated" is used similarly.

In many situations it is desirable to coat an active substance in such a way that the active substance is released from the coating only after a predetermined interval or only after a change in environment. For example, pesticides may be microencapsulated in 10 μm polyurea-polyamide coatings, which gradually degrade when applied to a surface, thereby gradually releasing the pesticide. In a medical context, it is particularly advantageous to be able to administer orally a medicament which is coated so that it passes through the stomach and is released only when the coated material reaches the small intestine. Such coatings are called "enteric" coatings and are relatively easy to formulate taking advantage of the fact that the stomach contents are acid and the intestinal contents are alkaline.

A harder task has been to provide a coated medicament which will survive both the stomach and the small intestine and will release the active ingredient only when the material reaches the large intestine or colon.

Many diseases of the colon, for example ulcerative colitis and Crohn's disease and potentially also cancer of the colon, could be better treated if site-specific delivery of the therapeutic agent could be effected. Therapeutic agents include corticosteroids, for example hydrocortisone and prednisolone, mesalazine, bisocodyl, phenolphthalein, rhein, sulphasalazine, cholestyramine and azathioprine. Few effective oral therapies are available, and administration via the rectum is messy and relatively expensive. If drugs for the treatment of colonic disease are encapsulated in an enteric coating, absorption of the drug from the small intestine is very rapid, and only small amounts of the drug reach the required site of action. If site-specific release could be obtained, smaller doses would be required, with a reduction in undesirable side effects.

There are also situations other than the treatment of diseases of the colon where it is desirable to deliver a drug to the colon before it is released. Thus, in certain conditions such as arthritis the release of drugs in the ileum can cause problems and it is desirable for laxatives and anti-diarrhoeal drugs to be selectively released in the colon. Other drugs may also benefit from such a form of release depending upon their absorption characteristics.

A number of approaches have been suggested for site-specific release to the colon. Thus, glycoside derivatives of steroid drugs are reported to be poorly absorbed in the stomach and small intestine but to be released in the large intestine through microbial action (Friend, D. R. and Chang, G. W., J. Med. Chem., 1984, 27, 261). Moreover, coating of peptide drugs with polymers cross-linked with azoaromatic groups is reported to protect the drugs from digestion in the stomach and small intestine but allow their release in the large intestine by the action of the indigenous microflora to effect reduction of the azo bonds (Saffron, M. et al., Science, 1986, 233, 1081).

It has now been found that certain types of amylose coatings are particularly suitable for the purpose of site-specific release in the colon. For a long time it was thought that starch was almost entirely degraded by α-amylase, a digestive enzyme present in the small intestine, but recently it has been reported in papers concerned with studies on foodstuffs that a proportion of starch is not degraded until it reaches the colon (Englyst and Cummings, Cereals in a European Context, edited by Morton, First European Conference on Food Science and Technology, Ellis Harwood, Chichester, England, 1987, page 221 and Ring et al, Food Chemistry, 1988, 28, 97).

However, papers concerned with the use of starch materials in a medical context have reported that amylose acts as an enteric coating, i.e. is not dissociated in the stomach but is dissociated in the small intestine. Thus Wagner et al, J. Am. Pharm. Assoc., 1959, 48, 244, disclose that acetate phthalate derivatives of starch and amylose are suitable for use as enteric coatings and Langlois and Wagoner, "Production and Use of Amylose", in "Starch Chemistry and Technology", Vol. II, Eds. R. L. Whistler and E. F. Paschall, Academic Press, 1965, 451 disclose that amylose and its derivatives are suitable for formulating pharmaceutical compositions but state that amylose disintegrates readily in contact with gastric liquids.

The present invention is based on the finding that glassy amylose can be used for the site-specific delivery of material into the colon. This is a very surprising result because of the previous indications that amylose could be used as an enteric coating and dissociates under the aqueous alkaline conditions of the small intestine. Moreover, for a material to be used to provide selective release of a compound into the colon requires a very great degree of selectivity as between the diverse group of digestive enzymes present in the stomach and the small intestine, and the enzymes present in the colon. It is particularly surprising that any form of amylose is capable of resisting the enzymes released from the pancreas yet is susceptible to those provided by the microbial flora of the colon.

Glassy amylose is one of the two forms of predominantly amorphous amylose, the other being a rubbery form. Amylose exists in its glassy state below the glass transition temperature (Tg). Rising through this temperature, there is a sharp increase in the heat capacity of the amylose of $0.5 \pm 0.15$ $Jg^{-1}K^{-1}$ (joules per gram per degree Kelvin). This heat capacity increment allows the Tg to be identified and can be measured by differential scanning calorimetry. (Examples of procedures for obtaining Tg values and earlier literature references to such procedures are given in Orford et al, Int. J. Biol. Macromol., 1989, 11, 91.)

The particular Tg of a given preparation of amylose depends upon its purity and other properties. Thus, for example, the theoretical Tg for pure, dry amylose may be predicted to be 210° C. but the presence of water depresses this figure: with 10% w/w of water the Tg is 80° C. and at 20% w/w of water it is 7° C. It has been found that α-amylolytic enzymes do not readily degrade glassy amylose and this effect is still apparent at up to 20° C. above the Tg. Such materials have been found to be sufficiently insoluble in aqueous media over the pH range 1-9 at 37° C. not to be significantly degraded in the stomach or intestine. They are, however, degraded by faecal micro-organisms present in the colon.

Thus, in one aspect the present invention provides a delayed release formulation of an active compound and amylose. In particular, a delayed release composition according to the present invention comprises an active compound and glassy amylose, the glassy amylose delaying the release of the active component from the composition in an aqueous environment but allowing its release on exposure to an enzyme capable of cleaving the amylose.

As indicated, the ability of glassy amylose to provide the required delayed release characteristics is not lost immediately the glassy amylose passes through the Tg and amylose which has been produced in the glassy condition at temperatures less than the Tg may therefore then be utilised at the Tg or at temperatures slightly higher than the Tg as well as at temperatures less than the Tg, whilst still retaining its glassy properties. However, the glassy amylose used in the present invention preferably has a Tg of no more than 20° C. below the temperature at which use of the composition is envisaged. The ultimate test of the suitability of a particular sample of amylose under any given conditions is of course its ability to resist hydrolytic degradation under aqueous conditions, particularly at a pH of 1–9 and a temperature of 37° C., and conveniently also to resist enzymatic degradation in the presence of the digestive enzymes such as normally occur in the stomach and the small intestine, but to undergo enzymatic degradation in the presence of amylose-cleaving enzymes such as are provided by the microbial flora normally present in the large intestine (see tests described in Example 1).

The amylose may conveniently be prepared in a glassy form either by forming a gel from an aqueous solution and then drying it or by spray drying. In the former process, the solution is conveniently 1.5–40% w/w amylose, preferably 3 to 30%, more preferably 4 to 20% and most preferably 6 to 10%, and is conveniently cooled from 70°–95° C., preferably 88°–92° C., to 0° to 40° C., preferably 5° to 35° C., most preferably 10° to 30° C., at a rate of $10^{-3}$° to $10^{5}$° C./second, preferably 0.1° to 1.0° C./second. Generally speaking, the cooling should take place over a period of hours, preferably 2 hours or less, rather than days, in order to prevent too much crystallisation, although some degree of crystallisation is acceptable, for example 20% or particularly 10%, or less. The gel forms by a phase separation which produces a concentrated polymer-rich phase and a polymer-poor phase. The polymer-rich phase may have only, say, 10% w/w water and hence be glassy at room temperature, even though the whole gel may contain over 90% w/w water. The whole preparation may be dried, if necessary or desirable, at 0°–160° C., preferably 20°–100° C. and more preferably about 60° C. in air or an inert atmosphere, for example nitrogen, or in vacuo in order to give a glassy or more glassy product.

The dry glassy amylose may be melted in the form of a slab or film or may first be powdered or granulated. Such melting is assisted if the Tg is depressed with a suitable diluent such as water. The melted amylose can then be used to coat preparations of active compound.

Alternatively, an aqueous solution of amylose, preferably 1–15%, suitably 2–10% and advantageously about 2 to 3% w/w, is sprayed directly onto a formulation containing an active compound and allowed to dry in air, in an inert atmosphere, for example nitrogen, or in vacuo to the glassy form. A further variation is for the aqueous solution to be sprayed as described onto a suitable inert support or into a sufficiently large volume of air or inert gas to form a glassy film or glassy particles which are then melted and used to coat the active compound formulation as above.

Generally speaking, the moisture content of the glassy amylose should be as low as possible. Conveniently, therefore, it does not exceed 20% (w/w) and preferably is less than this, for example being no more than 10, 5 or 1% (w/w).

In both the gel-forming and spraying processes, it is possible to include dispersions or solutions of suitable active compounds in the amylose solution itself, so that the resulting glassy form actually comprises the drug. It may be particularly advantageous to injection mould an amylose solution containing an active compound to form solid glassy pellets.

The amylose may be prepared from any suitable source although it is preferably prepared from starch, for example cereal starch or tuber starch but particularly starch from pulses, for example smooth-seeded pea starch, conveniently by precipitation from aqueous solution as a complex with an alcohol, for example 1-butanol, methanol, ethanol, propan-1-ol, propan-2-ol, pentanol, 2-methylbutan-2-ol or 2-methylbutan-1-ol as described by Ring et al, Macromolecules, 1985, 18, 182. The alcohol may conveniently then be removed from an aqueous dispersion of that complex by blowing through a suitable heated inert gas, for example nitrogen.

It will be appreciated that the presence of other materials in admixture with the glassy amylose will detract from the selective nature of the degradation of this material as between the stomach and small intestine and the large intestine. It is preferred therefore that the glassy amylose is substantially free (i.e. contains no more than 20% by weight and preferably no more than 10% or 5% by weight) of any material which is susceptible to digestion in the stomach or small intestine. In particular the glassy amylose preferably contains no more than 10% or 5% by weight of amylopectin, for example 1 or 2% or less, and conveniently also of any material containing glucoside linkages of the type found in amylopectin.

Moreover it is preferred that the glassy amylose does not contain hydroxy groups in derivative form and, if any derivativization is present that this is conveniently to an extent of no more than 10% of the hydroxy groups present, in particular no more than 4 or 5% and particularly 1 or 2% or less.

A convenient test for the purity of the amylose is provided by its iodine binding ability in a standard assay procedure such as is described by Banks et al, Starke, 1971, 23, 118. Thus pure, underivativized amylose binds with iodine to a level of about 19.5% w/w (i.e. 19.5±0.5% w/w) whereas the other main starch polysaccharide, amylopectin, binds less than 2.0% w/w and derivativization of the amylose will also reduce this binding ability. Conveniently therefore the amylose used in the present invention binds with iodine to a level of 15.0%±0.5% w/w or above, preferably to a level of 18.0%±0.5% w/w or above, and particularly to a level of 19.5±0.5% w/w.

The molecular weight of the modified amylose of the invention may conveniently be at least 20000 g/mol (or daltons) and is preferably higher so that it is advantageous to use amylose with a molecular weight of at least 100000, 200000, 300000, 400000 or 500000 g/mol depending on the particular circumstances.

The term "active compound" is used herein to denote a human or veterinary medicament, or a disinfectant, insecticide, acaricide, herbicide, plant growth regulator, animal behaviour modifier, deodorant, dye, chemical intermediate or reactant or any other compound of which one wishes to delay the release pending exposure to enzyme action, particularly by enzymes derived from micro-organisms. A particularly valuable aspect of the present invention is to provide a coated, or otherwise protected, medicament which may be administered orally for release in the colon as discussed above. In addition to such therapeutic use, the invention is also of particular interest in a diagnostic context, for example in delivering agents such as contrast media to the colon in connection with X-ray and NMR imaging techniques. An alternative diagnostic area lies in the delivery of potentially allergenic foodstuff components to the colon for the diagnosis of allergies.

Other areas of use involve pesticides such as a pyrethroid, for example permethrin, cypermethrin or deltamethrin, organochlorine or organophosphate which may be coated, or otherwise protected, for delayed release following exposure to micro-organisms in the environment, for example in the soil. A disinfectant (biocide or microbicide) may be kept inside such an amylose coating in a water storage or treatment plant and will be released only when micro-organisms, for example faecal micro-organisms, are present in significant quantities. Alternatively, a warning dye might be released in a similar manner. A further potential use of glassy amylose is as biodegradable packaging and various research uses can also be envisaged for the invention.

It will be appreciated that the active compound may be mixed with other carrier materials suitable to its particular use. Thus, for therapeutic use, the active compound will often be mixed with one or more of a bulking agent and a lubricant, for example lactose and magnesium stearate, respectively. Dosages of active compounds for therapeutic use will be as disclosed in the literature, for example in the ABPI Data Sheet Compendium, or may sometimes be less owing to the more efficient delivery of the compound.

The preferred Tg of the amylose will depend upon the intended use of the formulation. In a medical context, the Tg will conveniently be not more than 20° C. below 37° C., i.e. more than or equal to 17° C., and is preferably more than or equal to about 30° C. or, more preferably, more than or equal to about 40° C. For delayed release of a pesticide in a temperate climate, the Tg will conveniently exceed 0° C. and preferably exceed about 10° or 20° C.

The Tg of the amylose can be predetermined by controlling the amount of water in it. This can be achieved by varying the concentration of the amylose solution which is cooled or sprayed, and by drying the resulting gel. Drying also has the effect of reducing the pore size and hence permeability of the gel, which can be advantageous. A fatty or waxy substance such as carnauba wax may also conveniently be added to retard penetration of water where this is desirable.

As well as providing a delayed release the glassy amylose compositions of the present invention may also be used to provide a controlled release of an active compound both in the colon and in various other environments. Thus, variation in the physical nature of the amylose, for example as just described, will affect the rate of metabolism of the amylose by micro-organisms. Moreover, different particles of the active compound may be coated with coatings of differing thicknesses so that phased or gradual release can be achieved in response to a constant exposure to micro-organisms. The actual thicknesses can be arrived at by routine and non-inventive experimentation, but by way of assistance it may be indicated that a thickness of at least about 10 $\mu$m (including any other coating which may be present) is usually needed in order to ensure adequate mechanical strength. Where appropriate, the coating may not consist entirely of amylose since providing the nature and location of the amylose allow release or exposure of the contents under the desired circumstances. For example, the amylose can provide a "window" in an inert coating, or can provide temporary strength to an otherwise weak inert coating. The coated compound of the invention may be further coated with a conventional gelatin or enteric coating, optionally with a further active compound sandwiched between the two coatings. Thus, one can provide for respective drug release in the stomach and/or small intestine as well as in the colon. The material which is coated may be a solid, or an aqueous or non-aqueous liquid provided only that it does not degrade the amylose, or at least does not degrade it at an undesirable rate.

The glassy amylose need not necessarily be located as a coating in relation to the active compound in order to delay its release. Thus, as an alternative to its use in coating, the glassy amylose may be mixed with the active component, conveniently to produce a matrix throughout which the active component is dispersed. Such a composition may have a powder form or the powder may be compressed to form a monolith or formed solid. In particular particles of glassy amylose may be compressed with active compound particles into a tablet, instead of the active compound being coated with the glassy amylose.

In general, however, the glassy amylose and the active compound will not be in uniform admixture and in the preferred aspect of the invention the surface of the composition will comprise, in part or preferably substantially entirely, a layer of glassy amylose which is substantially free (i.e. contains 20% or less by weight and preferably 10% or 5% or less by weight) from the active compound.

EXAMPLE 1

Glassy Amylose Preparation

The starch polysaccharide amylose, an essentially linear polymer composed of $\alpha$-1,4-linked D-glucose, was isolated from smooth-seeded pea starch and purified by precipitation from aqueous solution as a complex with n-butanol. The isolated amylose had a weight average molecular weight of 500,000 g/mol. Concentrated aqueous solutions of amylose were regenerated from aqueous dispersions of the complex by removal of the n-butanol in a heated nitrogen stream. A 7% w/w aqueous solution of the amylose was cast as a gel slab $1.1 \times 10^{-3}$ m thick by rapidly quenching the amylose solution, held between glass plates, from 90° C. to 20° C. The gel was removed from the glass plates and allowed to dry overnight at room temperature. The resulting film had a thickness of $6 \times 10^{-5}$ m.

In vitro enzyme digestion

An amylose film prepared as just described was found to be insoluble in aqueous media over the pH range 1-9 at 37° C. The amylose film was also incubated at 37° C. in 0.05M phosphate buffer (pH 6.9) containing 0.04% w/v NaCl with a crystalline pancreatic α-amylase (25 units/mg polysaccharide). After a three day incubation period less than 10% by weight of the film had been solubilised.

In vitro microbial digestion

An amylose film prepared as just described was incubated at 37° C. with a mixed faecal inoculum of microorganisms under a carbon dioxide atmosphere, the initial density of micro-organisms being $1 \times 10^7$/ml. After 24 hours the film had lost approximately 50% of its weight, and after 48 hours the film had disintegrated.

EXAMPLE 2

Medicament formation (A) A 3% w/w aqueous solution of amylose, prepared as described in Example 1, is sprayed at a temperature of 90° C. onto a conventional tablet formulation of sulphasalazine comprising 50 mg of sulphasalazine[4-hydroxy-4'-(2-pyridyl-sulphamoyl)-azobenzene-3-carboxylic acid] in admixture with lactose and magnesium stearate and the wet tablet is then dried in a heated air stream at 100° C. to a moisture content of 0.2% w/w. About 50 μl of solution gives a 10 μm thick film.

To provide a 10 μm film on a similar conventional tablet formulation comprising 500 mg of sulphasalazine 100 μl of the same solution is required.

(B) A 3% w/w aqueous solution of amylose, prepared as described in Example 1, is sprayed at a temperature of 90° C. onto a tablet comprising 500 mg of mesalazine (5-aminosalicylic acid) in admixture with lactose and magnesium stearate and the wet tablet is then dried in a heated air stream at 100° C. to a moisture content of 0.2% w/w.

(C) A 3% w/w aqueous solution of amylose, prepared as described in Example 1, is sprayed at a temperature of 90° C. onto a tablet comprising 20 mg of either hydrocortisone or prednisolone in admixture with lactose and magnesium stearate and the wet tablet is then dried in a heated air stream at 100° C. to a moisture content of 0.2% w/w.

We claim:

1. A delayed release composition, comprising glassy amylose and a therapeutically or diagnostically active compound in an amount sufficient to exert a beneficial effect via the human large intestine and colon, for delivery to a microbial environment in the human large intestine and colon, said glassy amylose delaying release of the active compound from the composition in an aqueous environment of pH 1-9 at 37° C. and allowing its release on exposure to microbial amylase present in said microbial environment.

2. A delayed release composition according to claim 1 and being in powder form.

3. A delayed release composition according to claim 1 and having a monolithic form.

4. A delayed release composition according to claim 1, in which said therapeutically or diagnostically active compound is selectively released into the colon following oral administration of the composition.

5. A delayed release composition according to claim 1, in which said therapeutically active compound is a medicament for treatment of a disease of the colon.

6. A method for the treatment of a disease of the human colon, said method comprising the step of administering orally to a patient in need of such treatment a therapeutically effective amount of a delayed release composition comprising glassy amylose and a therapeutically active compound in an amount sufficient to exert a beneficial effect via the human large intestine and colon, for delivery to a microbial environment in the human large intestine and colon, said glassy amylose delaying release of therapeutically active compound from the composition in an aqueous environment of pH 1-9 at 37° C. and allowing its release on exposure to microbial amylase present in said microbial environment.

7. A method according to claim 6, in which the disease is ulcerative colitis.

8. A method according to claim 7, in which the disease is Crohn's disease.

9. A method according to claim 7, in which the disease is cancer.

* * * * *